US006180634B1

(12) United States Patent
Vacca et al.

(10) Patent No.: US 6,180,634 B1
(45) Date of Patent: Jan. 30, 2001

(54) COMBINATION THERAPY FOR THE TREATMENT OF AIDS

(75) Inventors: Joseph P. Vacca, Telford; Jiunn H. Lin, Ambler; Kuang C. Yeh, Lansdale, all of PA (US); Paul J. Deutsch, Princeton; William D. Ju, Morris Township, both of NJ (US); Jeffrey A. Chodakewitz, Lower Gwynedd, PA (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/191,895

(22) Filed: Nov. 13, 1998

Related U.S. Application Data

(60) Provisional application No. 60/065,421, filed on Nov. 13, 1997, and provisional application No. 60/090,940, filed on Jun. 26, 1998.

(51) Int. Cl.$^7$ .................. A61K 31/495; A61K 31/50; A61K 31/34
(52) U.S. Cl. ................ 514/254.11; 514/255; 514/473
(58) Field of Search .................. 514/473, 255, 514/254.11

(56) References Cited

U.S. PATENT DOCUMENTS

| | | | |
|---|---|---|---|
| 5,413,999 | 5/1995 | Vacca et al. | 514/231.5 |
| 5,567,823 | * 10/1996 | Tien et al. | 548/209 |
| 5,585,397 | * 12/1996 | Tung et al. | 514/473 |
| 5,646,148 | 7/1997 | Huff et al. | 514/253 |
| 5,750,493 | * 5/1998 | Sommadussi et al. | 514/1 |

FOREIGN PATENT DOCUMENTS

| | | | |
|---|---|---|---|
| 0 691 345 | 10/1996 | (EP) | C07K/5/02 |
| 95/16688 | 6/1995 | (WO) | C07D/473/00 |
| 95/33464 | 12/1995 | (WO) | A61K/31/475 |
| 97/01349 | 1/1997 | (WO) | A61K/38/06 |

OTHER PUBLICATIONS

Toh, H. et al., "Close structural resemblance between putatuve polymerase of a Drosophila transposable genetic element 17.6 abd pol gene product of Moloney murine leukaemia virus", The EMBO Journal, vol. 4, No. 5, pp. 1267–1272, 1985.

Ratner, L. et al., "Complete nucleotide sequence of the AIDS virus, HTLV–III", Nature, vol. 313, pp. 277–284, 1985.

Pearl, L. H. et al., "A structural model for retroviral proteases", Nature, vol. 329, pp. 351–354, 1987.

Kohl, N. E. et al., "Active human immunodeficiency virus protease in required for viral infection", Proc. Natl. Acad. Sci. USA, vol. 85, pp. 4686–4690, 1988.

Power, M.D. et al., "Nucleotide sequence of SRV–1, a type D Simian acquired immune deficiency syndrome retrovirus", Science, Vol. 231, pp. 1567–1572, 1986.

Kilby, J. M., et al., "Treatment of HIV–1 Infection—An Overview of New Strategies and Novel Agents", Infections in Medicine, vol. 13, No. 10, pp. 903–911 (1996).

Fischl, M. A., "Combination Antiretrovirial Therapy for HIV Infection", Hospital Practice, pp. 43–48 (Jan. 15, 1994).

Jablonowski, H., et al., "Antiretroviral Combination Therapy", AIDS Forschung, vol. 9, No. 11, pp. 563–567 (1994) (English Translation, copy of original enclosed, too).

Vella, S., et al., "Combination Therapy in the Management of HIV Infection", Meth. Find. Exp. Clin. Pharmacol., vol. 18, No. Suppl C, pp. 23–26 (1996).

Johnson, V., "Combination therapy for HIV–1 infection–overview: preclinical and clinical analysis of anti-retroviral combinations", Antiviral Research, vol. 29, pp. 35–39 (1996).

* cited by examiner

*Primary Examiner*—Russell Travers
(74) *Attorney, Agent, or Firm*—Kenneth R. Walton; Melvin Winokur

(57) ABSTRACT

The combination of the HIV protease inhibitor Compound A and one or more nucleoside reverse transcriptase inhibitors, non-nucleoside reverse transcriptase inhibitors, or protease inhibitors is useful in the inhibition of HIV protease, the inhibition of HIV reverse transcriptase, the prevention or treatment of AIDS, either as compounds, pharmaceutically acceptable salts or esters, pharmaceutical composition ingredients, whether or not in combination with other antivirals, immunomodulators, antibiotics or vaccines. Methods of treating AIDS and methods of preventing or treating infection by HIV are also described.

20 Claims, No Drawings

COMBINATION THERAPY FOR THE TREATMENT OF AIDS

CROSS REFERENCE TO RELATED APPLICATIONS

This application claims the benefit of U.S. Provisional Application No. 60/065,421, filed Nov. 13, 1997 and U.S. provisional Application No. 60/090,940, filed Jun. 26, 1998.

FIELD OF THE INVENTION

The present invention provides combination therapy for the treatment of HIV infection and AIDS. More particularly, the combination comprises an HIV protease inhibitor, Compound A, with one or more nucleoside reverse transcriptase inhibitors, non-nucleoside reverse transcriptase inhibitors, or protease inhibitors.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., Proc. Nat'l Acad. Sci., 85, 4686 (1988), demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, an endonuclease and an HIV protease [Toh, H. et al., EMBO J., 4, 1267 (1985); Power, M. D. et al., Science, 231, 1567 (1986); Pearl, L. H. et al., Nature, 329, 351 (1987)].

The compound N-(2(R)-hydroxy-1(S)-indanyl)-2(R)-phenylmethyl-4-(S)-hydroxy-5-(1-(4-(2-benzo[b]furanylmethyl)-2(S)-N'-(t-butylcarboxamido)-piperazinyl))-pentaneamide disclosed in U.S. Pat. No. 5,646,148, issued Jul. 8, 1997, and referred to herein as "Compound A," is a potent inhibitor of HIV protease and is useful in the prevention of infection by HIV, the treatment of infection by HIV and the treatment of AIDS or ARC (AIDS related complex), without significant side effects or toxicity.

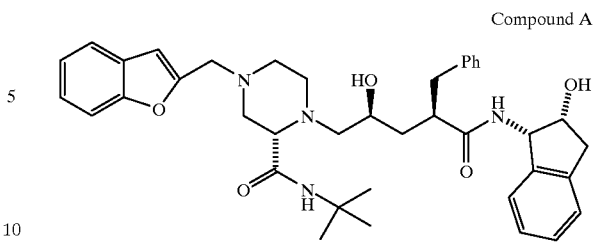

Compound A

One substantial and persistent problem in the treatment of AIDS has been the ability of the HIV virus to develop resistance to the individual therapeutic agents employed to treat the disease. Thus, a need remains for an efficacious and long lasting therapy for AIDS which lowers HIV viral levels of patients to undetectable levels and raises CD4 cell counts for prolonged periods of time without the development of resistance. Therefore, it is an object of the invention to provide a combination therapy which lowers HIV viral levels below the limit of detection. It is another object of the invention to increase the count of CD4 cells for prolonged periods of time. Furthermore, it is an object of the invention to achieve both of these favorable results for extended periods of time without the development of resistance to the therapies.

Applicants have discovered that the combinations of this invention are effective inhibitors of HIV protease. In the present invention, Applicants co-administer a potent HIV protease inhibitor, Compound A, or pharmaceutically acceptable salts or esters thereof, with one or more nucleoside reverse transcriptase, non-nucleoside reverse transcriptase inhibitors, or protease inhibitors. Optionally, Compound A, or pharmaceutically acceptable salts or esters thereof, is co-administered with Zidovudine and Lamivudine. This combination therapy is a method to enhance the effectiveness in treating AIDS and to preclude the development of resistance to the individual therapeutic agents.

SUMMARY OF THE INVENTION

The instant invention involves a composition comprising Compound A of the formula

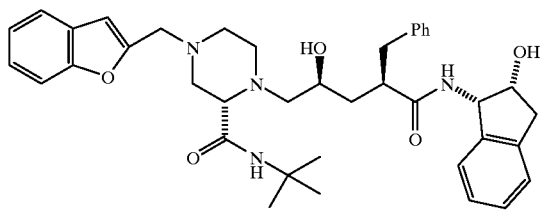

and one or more antiretroviral agents selected from Zidovudine, Lamivudine, Stavudine, DMP-266, Ritonavir, Nelfinavir, Abacavir, Indinavir, 141-W94, Delavirdine, or Saquinavir; and pharmaceutically acceptable salts or esters thereof.

In one embodiment of the instant invention is the composition comprising Compound A and one, two, or three antiretroviral agents selected from Zidovudine, Lamivudine, Stavudine, DMP-266, Ritonavir, Nelfinavir, Abacavir, Indinavir, 141-W94, or Delavirdine; and pharmaceutically acceptable salts or esters thereof.

In a class of the instant invention is the composition comprising Compound A and one or two of the above mentioned antiretroviral agents; and pharmaceutically acceptable salts or esters thereof.

In a subclass of the instant invention is the composition comprising Compound A and one of the above mentioned antiretroviral agents.

Preferred embodiments of the instant invention include the compositions comprising: (1) Compound A, Zidovudine and Lamivudine; (2) Compound A, Stavudine and Lamivudine; (3) Compound A and DMP-266; (4) Compound A and Ritonavir; (5) Compound A and Nelfinavir; (6) Compound A and Abacavir; (7) Compound A and Indinavir; (8) Compound A and 141-W94; (9) Compound A and Delavirdine.

Another preferred embodiment of the invention is a composition comprising (a) Compound A or a pharmaceutically acceptable salt or ester thereof and (b) a compound selected from the group consisting of Indinavir, Ritonavir, Nelfinavir, Delavirdine, 141-W94, and pharmaceutically acceptable salts and esters thereof. Compound (b) is preferably selected from the group consisting of Indinavir, Ritonavir, and pharmaceutically acceptable salts thereof, and is most preferably Indinavir or a pharmaceutically acceptable salt or ester thereof. Particularly preferred is the composition in which (a) is the sulfate salt of Compound A and (b) is the sulfate salt of Indinavir. It has been discovered that the foregoing compounds of (b), when employed in combination with Compound A, can increase the plasma concentration of Compound A to a level having substantial antiviral activity. Compound A is a potent protease inhibitor, exhibiting approximately two-fold greater potency than Indinavir against wild type HIV-1 and a similar potency with respect to other HIV-1 variants in in vitro assays (e.g., CIC95 of Compound A=25 nM against wild-type HIV-1 versus 50 nM of Indinavir, as determined by the Cell Spread Assay described in U.S. Pat. No. 5,646,148). It was unexpectedly found, however, that the administration of Compound A to humans resulted in very low plasma concentrations of Compound A relative to concentrations achieved from administration of comparable doses of Indinavir. Furthermore, pharmacokinetic studies in human subjects have resulted in significant inter-individual variation in the plasma levels of Compound A, a variation much greater than that observed for Indinavir.

The problems of low plasma concentration and of high inter-individual plasma level variation encountered with the administration of Compound A have been solved by the co-administration of Compound A with Indinavir. This solution was arrived at as a result of the following findings:

(i) Compound A has a low affinity for CYPIIIA4, the enzyme which metabolizes it; i.e., the IC50 of Compound A for in vitro inhibition of CYPIIIA4=30 micromolar. In contrast, Indinavir has a comparatively very high affinity for CYPIIIA4 (IC50=0.2 micromolar).

(ii) In addition to the unexpectedly very low plasma concentrations noted above for Compound A relative to those achieved with comparable doses of Indinavir, it was also unexpectedly found that the administration of successively higher doses of Compound A to humans resulted in greater than proportional increases in plasma concentrations.

These findings led to the theory that the very low plasma concentrations and high intersubject variability of Compound A achieved following administration to humans was due to extensive metabolism by CYPIIIA4 prior to entry of drug into the systemic circulation. This in turn led to the hypothesis that the concomitant administration of another compound with higher affinity for CYPIIIA4 such as Indinavir could inhibit the metabolism of Compound A to the degree that plasma concentrations of Compound A would be increased, thereby providing plasma concentrations of Compound A having substantial antiviral activity. While not wishing to be bound by the foregoing theory and hypothesis, it has in fact been discovered that use of Indinavir in combination with Compound A does substantially increase the plasma concentrations of Compound A and also markedly reduces inter-individual variation thereof.

Ritonavir, Nelfinavir, Delavirdine, and 141-W94 can also act as inhibitors of CYPIIIA, and thus can inhibit the metabolism of Compound A, thereby resulting in increased plasma levels and reduced inter-individual variation for Compound A.

A further particularly preferred embodiment of the invention is a composition comprising (a) Compound A or a pharmaceutically acceptable salt or ester thereof and (b) Indinavir or a pharmaceutically acceptable salt or ester thereof, wherein the composition has a weight ratio of Compound A to Indinavir ranging from about 15:1 to about 1:15. In other embodiments, the weight ratio of Compound A to Indinavir is from about 1:10 to about 10:1, or from about 8:1 to about 1:8, or from about 6:1 to about 1:6, or from about 4:1 to about 1:4, or from about 2:1 to about 1:2, or from about 1.5:1 to about 1:1.5.

In still another particularly preferred embodiment of the invention is a composition comprising (a) Compound A or a pharmaceutically acceptable salt or ester thereof and (b) Indinavir or a pharmaceutically acceptable salt or ester thereof, wherein the composition has a weight ratio of Compound A to Indinavir ranging from about 1:1 to about 10:1. In other embodiments, the weight ratio of Compound A to Indinavir is from about 1:1 to about 8:1, or from about 1:1 to about 6:1, or from about 1:1 to about 5:1, or from about 1:1 to about 4:1 (e.g., from about 3:2 to about 3:1), or from about 1:1 to about 2:1 (e.g., about 1.5:1), or from about 1:1 to about 1.5:1.

Other preferred embodiments of the instant invention include the compositions respectively comprising: (1) Compound A, Indinavir, Zidovudine and Lamivudine; (2) Compound A, Indinavir, Stavudine and Lamivudine; (3) Compound A, Indinavir and DMP-266; (4) Compound A, Indinavir and Delavirdine; and (5) Compound A, Indinavir and Saquinavir. In these embodiments, a pharmaceutically acceptable salt or ester can be substituted for any one or more of the compounds per se. In a further aspect of these embodiments, the weight ratio of Compound A to Indinavir can be any one of the weight ratios set forth in the preceding two paragraphs.

Exemplifying the invention is a method of preventing infection by HIV, or of treating infection by HIV, or of preventing or treating AIDS or ARC, comprising administering to a subject in need thereof a therapeutically effective amount of any of the compositions described above.

Further exemplifying the invention is a method of inhibiting HIV protease, comprising administering to a subject in need thereof a therapeutically effective amount of Compound A and one or more antiretroviral agents selected from Zidovudine, Lamivudine, Stavudine, DMP-266, Ritonavir, Nelfinavir, Abacavir, Indinavir, 141-W94, or Delavirdine; and pharmaceutically acceptable salts or esters thereof.

Further exemplifying the invention is a method of inhibiting HIV protease which comprises administering to a subject in need thereof a therapeutically effective amount of Compound A and Indinavir. In a further aspect of this method, the weight ratio of Compound A to Indinavir can be any one of the weight ratios set forth above. In yet another aspect of these methods, a pharmaceutically acceptable salt or ester can be substituted for any one or more of the compounds per se.

Still further examples of the invention include methods of inhibiting HIV protease, wherein the methods comprise administering to a subject in need thereof a therapeutically effective amount of, respectively, (1) Compound A, Indinavir, Zidovudine and Lamivudine; (2) Compound A, Indinavir, Stavudine and Lamivudine; (3) Compound A, Indinavir and DMP-266; (4) Compound A, Indinavir and Delavirdine; and (5) Compound A, Indinavir and Saquinavir. In a further aspect of these methods, a pharmaceutically acceptable salt or ester can be substituted for any one or more of the compounds per se. In yet another aspect of these methods, the weight ratio of Compound A to Indinavir can be any one of the weight ratios set forth above.

An example of the invention is a method of inhibiting HIV reverse transcriptase, comprising administering to a subject in need thereof a therapeutically effective amount of Compound A and one or more of the above mentioned antiretroviral agents.

Another example of the invention is a method of inhibiting HIV reverse transcriptase, comprising administering to a subject in need thereof a therapeutically effective amount of Compound A, Indinavir, and optionally Saquinavir, and one or more of Zidovudine, Stavudine, Lamivudine, DMP-266, Abacavir, and Delavirdine. In a further aspect of the method, a pharmaceutically acceptable salt or ester can be substituted for any one or more of the compounds per se. In yet another aspect of the method, the weight ratio of Compound A to Indinavir can be any one of the weight ratios set forth above.

An illustration of the invention is a method of preventing infection by HIV, or of treating infection by HIV, or of preventing or treating AIDS or ARC, comprising administering to a subject in need thereof a therapeutically effective amount of Compound A and one or more of the above mentioned antiretroviral agents.

More particularly illustrating the invention is a method of preventing infection by HIV, or of treating infection by HIV, or of treating AIDS or ARC, comprising administering to a subject in need thereof a therapeutically effective amount of Compound A, Zidovudine, and Lamivudine, or pharmaceutically acceptable salts or esters thereof.

Also illustrating the invention is a method of preventing infection by HIV, or of treating infection by HIV, or of treating AIDS or ARC, comprising administering to a subject in need thereof a therapeutically effective amount of Compound A and DMP-266, or pharmaceutically acceptable salts or esters thereof.

Further illustrating the invention is a method of preventing infection by HIV, or of treating infection by HIV, or of treating AIDS or ARC, comprising administering to a subject in need thereof a therapeutically effective amount of Compound A and Indinavir, or pharmaceutically acceptable salts or esters thereof.

Still further illustrating the invention is a method of preventing infection by HIV, or of treating the infection by HIV, or of treating AIDS or ARC, which comprises administering to a subject in need thereof a therapeutically effective amount of (a) Compound A or a pharmaceutically acceptable salt or ester thereof and (b) Indinavir or a pharmaceutically acceptable salt or ester thereof, wherein the composition has a weight ratio of Compound A to Indinavir ranging from about 15:1 to about 1:15. In other aspects of this method, the weight ratio of Compound A to Indinavir is from about 10:1 to about 1:10, or from about 8:1 to about 1:8, or from about 6:1 to about 1:6, or from about 4:1 to about 1:4, or from about 2:1 to about 1:2, or from about 1.5:1 to about 1:1.5.

In yet another illustration of the invention is a method of preventing infection by HIV, or of treating the infection by HIV, or of treating AIDS or ARC, which comprises administering to a subject in need thereof a therapeutically effective amount of (a) Compound A or a pharmaceutically acceptable salt or ester thereof and (b) Indinavir or a pharmaceutically acceptable salt or ester thereof, wherein the composition has a weight ratio of Compound A to Indinavir ranging from about 1:1 to about 10:1. In further aspects of this method, the weight ratio of Compound A to Indinavir is from about 1:1 to about 8:1, or from about 1:1 to about 6:1, or from about 1:1 to about 5:1, or from about 1:1 to about 4:1 (e.g., from about 3:2 to about 3:1), or from about 1:1 to about 2:1 (e.g., about 1.5:1), or from about 1:1 to about 1.5:1.

Still other illustrations of the invention include methods of preventing infection by HIV, or of treating the infection by HIV, or of treating AIDS or ARC, wherein the methods comprise administering to a subject in need thereof a therapeutically effective amount of, respectively, (1) Compound A, Indinavir, Zidovudine and Lamivudine; (2) Compound A, Indinavir, Stavudine and Lamivudine; (3) Compound A, Indinavir and DMP-266; (4) Compound A, Indinavir and Delavirdine; and (5) Compound A, Indinavir and Saquinavir. In a further aspect of the foregoing methods, a pharmaceutically acceptable salt or ester can be substituted for any one or more of the compounds per se. In yet another aspect of these methods, the weight ratio of Compound A to Indinavir can be any one of the weight ratios set forth above.

An example of the invention is a method of preventing infection by HIV, or of treating infection by HIV, or of treating AIDS or ARC, comprising administering to a subject in need thereof a therapeutically effective amount of Compound A, Stavudine, and Lamivudine, or pharmaceutically acceptable salts or esters thereof Exemplifying this invention is the use of Compound A and one or more antiretroviral agents selected from Zidovudine, Lamivudine, Stavudine, DMP-266, Ritonavir, Nelfinavir, Abacavir, Indinavir, 141-W94, or Delavirdine; and pharmaceutically acceptable salts or esters thereof, in the preparation of a medicament for the treatment of infection by HIV and/or for the treatment of AIDS which comprises an effective amount of Compound A and one or more of the above mentioned antiretroviral agents and pharmaceutically acceptable salts or esters thereof, together or separately.

Further exemplifying this invention is the use of Compound A or a pharmaceutically acceptable salt or ester thereof and Indinavir or a pharmaceutically acceptable salt or ester thereof in the preparation of a medicament for the treatment of infection by HIV and/or for the treatment of AIDS which comprises an effective amount of Compound A or a pharmaceutically acceptable salt or ester thereof and Indinavir or a pharmaceutically acceptable salt or ester thereof. In another aspect of this use, the weight ratio of Compound A to Indinavir in the medicament can be any one of the weight ratios set forth above. Another aspect is the use Compound A and Indinavir with one or more of the other antiviral agents as set forth above.

Specifically illustrating the invention is a pharmaceutical composition comprising Compound A and one or more antiretroviral agents selected from Zidovudine, Lamivudine, Stavudine, DMP-266, Ritonavir, Nelfinavir, Abacavir, Indinavir, 141-W94, or Delavirdine, and pharmaceutically acceptable salts or esters thereof, and a pharmaceutically acceptable carrier. Also included in the invention is a pharmaceutical composition made by combining Compound A and one or more of the above mentioned antiretroviral agents and pharmaceutically acceptable salts thereof, with a pharmaceutically acceptable carrier. Additionally, the present invention includes a process for making a pharmaceutical composition comprising combining Compound A, one or more of the above mentioned antiretroviral agents and a pharmaceutically acceptable carrier.

More specifically exemplifying the invention is a pharmaceutical composition comprising Compound A, Zidovudine, and Lamivudine, and pharmaceutically acceptable salts or esters thereof, and a pharmaceutically acceptable carrier.

Illustrative of the invention is a pharmaceutical composition comprising Compound A and DMP-266, and pharmaceutically acceptable salts or esters thereof, and a pharmaceutically acceptable carrier.

Further illustrating the invention is a pharmaceutical composition comprising Compound A and Indinavir, and pharmaceutically acceptable salts or esters thereof, and a pharmaceutically acceptable carrier.

Still further illustrating the invention is a pharmaceutical composition comprising (a) Compound A or a pharmaceutically acceptable salt or ester thereof; (b) Indinavir or a pharmaceutically acceptable salt or ester thereof; and (c) a pharmaceutically acceptable carrier; wherein the composition has a weight ratio of Compound A to Indinavir ranging from about 15:1 to about 1:15. Other illustrations of the invention include the pharmaceutical composition set forth in the preceding sentence, wherein the weight ratio of Compound A to Indinavir is from about 10:1 to about 1:10, or from about 8:1 to about 1:8, or from about 6:1 to about 1:6, or from about 4:1 to about 1:4, or from about 2:1 to about 1:2, or from about 1.5:1 to about 1:1.5.

In yet another illustration of the invention is a pharmaceutical composition comprising (a) Compound A or a pharmaceutically acceptable salt or ester thereof; (b) Indinavir or a pharmaceutically acceptable salt or ester thereof; and (c) a pharmaceutically acceptable carrier; wherein the composition has a weight ratio of Compound A to Indinavir ranging from about 1:1 to about 10:1. Other illustrations of the invention include a pharmaceutical composition as set forth in the preceding sentence, wherein the weight ratio of Compound A to Indinavir is from about 1:1 to about 8:1, or from about 1:1 to about 6:1, or from about 1:1 to about 5:1, or from about 1:1 to about 4:1 (e.g., from about 3:2 to about 3:1), or from about 1:1 to about 2:1 (e.g., about 1.5:1), or from about 1:1 to about 1.5:1.

Still other illustrations of the invention include the pharmaceutical compositions comprising, respectively, (1) Compound A, Indinavir, Zidovudine, Lamivudine and a pharmaceutically acceptable carrier; (2) Compound A, Indinavir, Stavudine, Lamivudine and a pharmaceutically acceptable carrier; (3) Compound A, Indinavir, DMP-266 and a pharmaceutically acceptable carrier; (4) Compound A, Indinavir, Delavirdine and a pharmaceutically acceptable carrier; and (5) Compound A, Indinavir, Saquinavir and a pharmaceutically acceptable carrier. In a further aspect of the foregoing compositions, a pharmaceutically acceptable salt or ester can be substituted for any one or more of the compounds per se. In yet another aspect of these compositions, the weight ratio of Compound A to Indinavir can be any one of the weight ratios set forth above.

Exemplifying the invention is a composition made by combining Compound A and one or more antiretroviral agents selected from Zidovudine, Lamivudine, Stavudine, DMP-266, Ritonavir, Nelfinavir, Abacavir, Indinavir, 141-W94, or Delavirdine; and a pharmaceutically acceptable salt or ester thereof.

Also exemplifying the invention is a process for making a composition comprising combining Compound A and one or more antiretroviral agents selected from Zidovudine, Lamivudine, Stavudine, DMP-266, Ritonavir, Nelfinavir, Abacavir, Indinavir, 141-W94, or Delavirdine; and a pharmaceutically acceptable salt or ester thereof.

Also exemplifying the invention is a process for making a composition which comprises combining (a) Compound A or a pharmaceutically acceptable salt or ester thereof; (b) Indinavir or a pharmaceutically acceptable salt or ester thereof; wherein the composition has a weight ratio of Compound A to Indinavir ranging from about 15:1 to about 1:15. In further aspects of the process, the weight ratio of Compound A to Indinavir is from about 10:1 to about 1:10, or from about 8:1 to about 1:8, or from about 6:1 to about 1:6, or from about 4:1 to about 1:4, or from about 2:1 to about 1:2, or from about 1.5:1 to about 1:1.5.

In yet another exemplification of the invention is a process for making a composition which comprises combining (a) Compound A or a pharmaceutically acceptable salt or ester thereof; (b) Indinavir or a pharmaceutically acceptable salt or ester thereof; wherein the composition has a weight ratio of Compound A to Indinavir ranging from about 1:1 to about 10:1. In further aspects of this process, the weight ratio of Compound A to Indinavir is from about 1:1 to about 8:1, or from about 1:1 to about 6:1, or from about 1:1 to about 5:1, or from about 1:1 to about 4:1 (e.g., from about 3:2 to about 3:1), or from about 1:1 to about 2:1 (e.g., about 1.5:1), or from about 1:1 to about 1.5:1.

DETAILED DESCRIPTION OF THE INVENTION

This invention is concerned with the combination of certain compounds, or pharmaceutically acceptable salts thereof, in the inhibition of HIV protease, the inhibition of HIV reverse transcriptase, the prevention or treatment of infection by HIV and in the prevention or treatment of the resulting acquired immune deficiency syndrome (AIDS). The combination is defined as follows:

Compound A and one or more antiretroviral agents selected from Zidovudine, Lamivudine, Stavudine, DMP-266, Ritonavir, Nelfinavir, Abacavir, Indinavir, 141-W94, or Delavirdine, or a pharmaceutically acceptable salt or ester thereof. Preferably, the combination comprises Compound A and one, two, or three of the antiretroviral agents. More preferably, the combination comprises Compound A and one or two of the antiretroviral agents.

The combination also includes Compound A, Indinavir, and Saquinavir, or a pharmaceutically acceptable salt or ester of one or more of the foregoing compounds.

The combinations of this invention can provide synergistic or other unexpected effects and benefits.

The term "Compound A" as used herein is N-(2(R)-hydroxy-1(S)-indanyl)-2(R)-phenylmethyl-4-(S)-hydroxy-5-(1-(4-(2-benzo[b]furanylmethyl)-2(S)-N'(t-butylcarboxamido)-piperazinyl))-pentaneamide, or a pharmaceutically acceptable salt thereof,

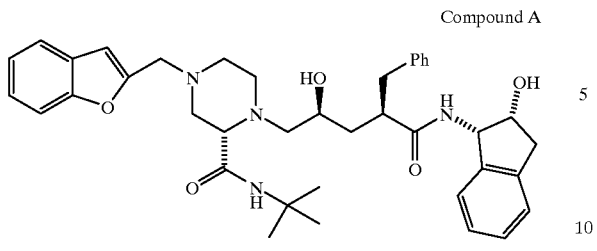

Compound A

Compound A and its utility as an HIV protease inhibitor is described in U.S. Pat. No. 5,646,148, issued Jul. 8, 1997. Compound A is synthesized by the protocol of U.S. Pat. No. 5,646,148 or by the procedure described in detail herein.

Zidovudine is 3'-Azido-3'-deoxythymidine, also known as AZT and RETROVIR®.

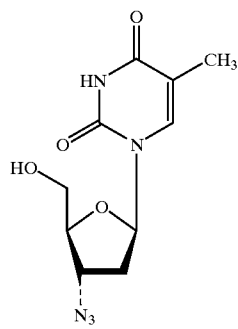

Zidovudine

Zidovudine is a nucleoside reverse transcriptase inhibitor currently used to treat AIDS. It is commercially available from Burroughs-Wellcome as RETROVIR®.

Stavudine is 2',3'-Didehydro-3'-deoxythymidine, also known as 2',3'-dihydro-3'-deoxythymidine, d4T, and ZERIT®.

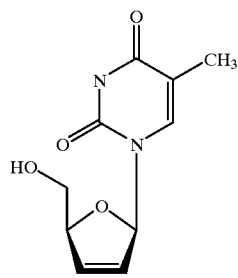

Stavudine is a nucleoside reverse transcriptase inhibitor currently used to treat AIDS. It is commercially available from Bristol-Myers Squibb as ZERIT®.

Lamivudine is (2R-cis)-4-Amino-1-[2-(hydroxymethyl)-1,3-oxathiolan-5-yl]-2(1H)-pyrimidinone, also known as (−)-1-[(2R,5S)-2-(Hydroxymethyl)-1,3-oxathiolan-5-yl] cytosine, 3TC, and EPIVIR®.

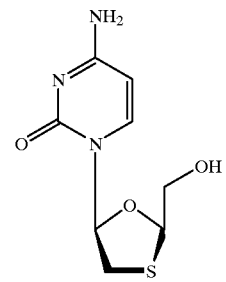

Lamivudine

Lamivudine is a nucleoside reverse transcriptase inhibitor currently used to treat AIDS. It is commercially available from Glaxo Wellcome as EPIVIR®.

DMP-266 is (−)-6-Chloro-4-cyclopropylethynyl-4-trifluoromethyl-1,4-dihydro-2H-3,1-benzoxazin-2-one, also known as efavirenz or SUSTIVA® or STOCRIN®.

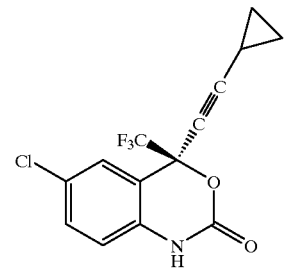

DMP-266

DMP-266 is a non-nucleoside reverse transcriptase inhibitor of HIV. DMP-266 and its utility as an HIV reverse transcriptase inhibitor is described in U.S. Pat. No. 5,519,021, issued May 21, 1996, and the corresponding PCT International Patent Application WO 95/20389, which published on Aug. 3, 1995. DMP-266 can be synthesized by the protocol of U.S. Pat. No. 5,633,405, issued May 27, 1997. Additionally, the asymmetric synthesis of an enantiomeric benzoxazinone by a highly enantioselective acetylide addition and cyclization sequence is described in Thompson, et al., Tetrahedron Letters 1995, 36, 8937–40, as well as in the PCT publication, WO 96/37457, which published on Nov. 28, 1996.

Ritonavir is [5S-(5R*,8R*, 10R*,11R*)]-10-Hydroxy-2-methyl-5-(1-methylethyl)-1-[2-(1-methylethyl)-4-thiazolyl]-3,6-dioxo-8,11-bis(phenylmethyl)-2, 4, 7, 12-tetraazatridecan-13-oic acid 5-thiazolylmethyl ester, also known as 5-Thiazolylmethyl [(aS)-a-[(1S,3S)-1-hydroxy-3-[(2S)-2-[3-[(2-isopropyl-4-thiazolyl)methyl]-3-methylureido]-3-methylbutyramido]-4-phenylbutyl] phenethyl]carbamate and NORVIR®.

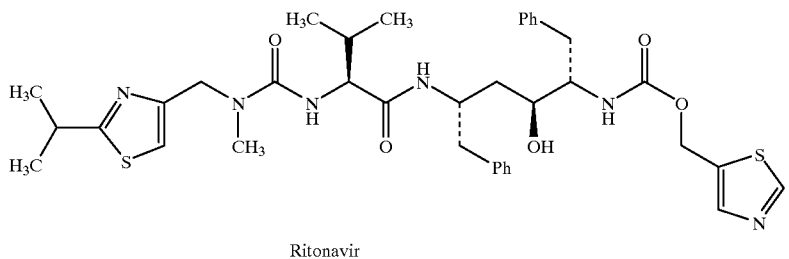

Ritonavir

Ritonavir is an HIV protease inhibitor currently used to treat AIDS. It is commercially available from Abbott as NORVIR®.

Nelfinavir is [3S-[2(2S*,3S*),3a,4ab,8ab]]-N-(1,1-dimethylethyl)decahydro-2-[2-hydroxy-3-[(3-hydroxy-2-methylbenzoyl)amino]-4-(phenylthio)butyl]-3-isoquinolinecarboxamide monomethanesulfonate, also known as (3S,4aS,8aS)-N-tert-Butyl-2-[(2R,3R)-3-(3,2-crestoamido)-2-hydroxy-4-(phenylthio)butyl]decahydro-3-isoquinolinecarboxamide monomethanesulfonate and VIRACEPT®.

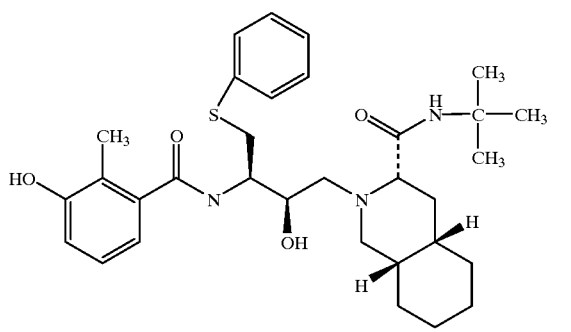

Nelfinavir

Nelfinavir is an HIV protease inhibitor that has received FDA approval to treat AIDS available from Agouron.

Abacavir is (1S,4R)-cis-4-[2-amino-6-(cycloprpoylamino)-9H-purin-9-yl]-2-cyclopentene-1-methanol, also known as 1592U89.

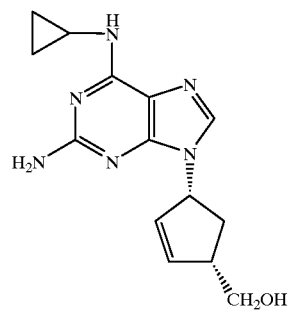

Abacavir

Abacavir is a non-nucleoside reverse transcriptase inhibitor currently under FDA investigation. Abacavir can be prepared by following the protocol of EP 0434450, published Jun. 26, 1991

Indinavir is N-(2(R)-hydroxy-1(S)-indanyl)2(R)-phenylmethyl-4-(S)-hydroxy-5-(1-(4-(3-pyridylmethyl)-2 (S)-N'-(t-butylcarboxamido)-piperazinyl))-pentaneamide, also known as CRIXIVAN®.

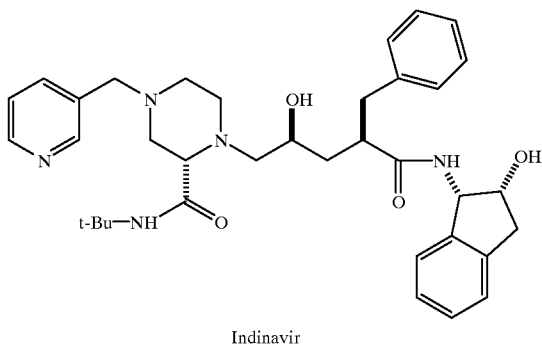

Indinavir

Indinavir is an HIV protease inhibitor currently used to treat AIDS. Indinavir is the active agent in CRIXIVAN® (indinavir sulfate) and is commercially available from Merck & Co., Inc.

141-W94 is 4-amino-N-((2 syn,3S)-2-hydroxy-4-phenyl-3-((S)-tetrahydrofuran-3-yloxycarbonylamino)-butyl)-N-isobutyl-benzenesulfonamide, also known as Compound 168 and amprenavir.

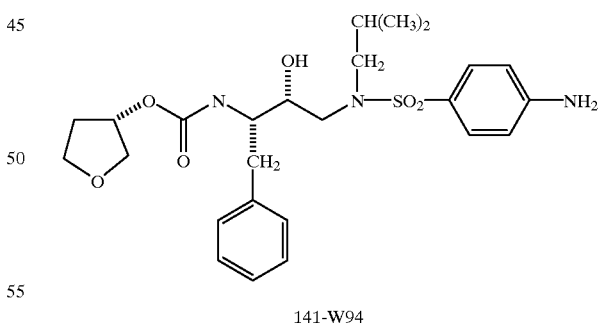

141-W94

141-W94 is an aspartyl protease inhibitor that can be prepared by following the procedures described in U.S. Pat. No. 5,585,397, issued Dec. 19, 1996.

Delavirdine is 1-[3-[(1-methylethyl)aminol]-2-pyridinyl]-4-[[5-[(methylsulfonyl)amino]-1H-indol-2-yl]carbonyl] piperazine, also known as U-90152.

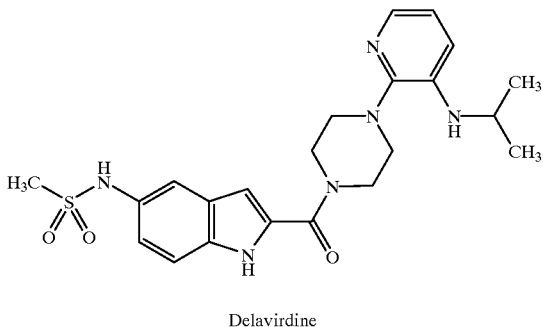

Delavirdine

Delavirdine is a non-nucleoside reverse transcriptase inhibitor that can be prepared according to the procedures described in PCT International Patent Application No. WO 91/09849, published Jul. 11, 1991.

Saquinavir is N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide, also known as INVIRASE®. Saquinavir is an HIV protease inhibitor approved by the FDA for use in the treatment of HIV infection. Saquinavir can be prepared in accordance with procedures disclosed in U.S. Pat. No. 5,196,438, issued Mar. 23, 1993. INVIRASE® (saquinavir mesylate) is available from Roche Laboratories.

In the methods of treatment of the present invention, the term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. Since the instant invention refers to compositions comprising two or more agents, the "therapeutically effective amount" is that amount of the combination of the agents taken together so that the combined effect elicits the desired biological or medicinal response. For example, the therapeutically effective amount of a composition comprising Compound A and DMP-266 would be the amount of Compound A and the amount of DMP-266 that when taken together have a combined effect that is therapeutically effective.

As used herein, the term "composition" is intended to encompass a product comprising the specified ingredients in the specified amounts, as well as any product which results, directly or indirectly, from combination of the specified ingredients in the specified amounts.

The pharmaceutically acceptable salts of the present invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

The pharmaceutically acceptable salts of the instant invention include the combination wherein one of the individual components is in the form of a pharmaceutically acceptable salt, the combination wherein all of the individual components are in the form of pharmaceutically acceptable salts, the combination wherein one or more of the individual components is in the form of a pharmaceutically acceptable salt while other of the components are used as the free base, or a pharmaceutically acceptable salt of the combined components (i.e., a salt of the combination). In one embodiment of the present invention, the sulfate salt of the combination is utilized.

The pharmaceutically acceptable esters in the present invention refer to non-toxic esters, preferably the alkyl esters such as methyl, ethyl, propyl, isopropyl, butyl, isobutyl, or pentyl esters, of which the methyl ester is preferred. However, other esters such as phenyl-C1-5 alkyl may be employed if desired.

Esterification of alcohols, such as Compound A of the present invention, is performed by a variety of conventional procedures, including reacting the alcohol group with the appropriate anhydride, carboxylic acid or acid chloride. These reactions, as well as other methods of esterification of alcohols, are readily apparent to the skilled artisan.

Reaction of the alcohol with the appropriate anhydride is carried out in the presence of an acylation catalyst, such as 4-DMAP (4-dimethylaminopyridine, also known as N,N-dimethylaminopyridine), pyridine, or 1,8-bis[dimethylamino]napthalene.

Reaction of the alcohol with the appropriate carboxylic acid is carried out in the presence of a dehydrating agent and, optionally, an acylation catalyst. The dehydrating agent, which serves to drive the reaction by the removal of water is selected from dicyclohexylcarbodiimide (DCC), 1-[3-dimethylaminopropyl]-3-ethylcarbodiimide (EDC) or other water soluble dehydrating agents.

Alternatively, reaction of the alcohol with appropriate carboxylic acid can also result in esterification, if performed instead in the presence of trifluoroacetic anhydride, and, optionally, pyridine. A further variant is reacting the alcohol with appropriate carboxylic acid in the presence of N,N-carbonyldiimidazole with pyridine.

Reaction of the alcohol with the acid chloride is carried out with an acylation catalyst, such as 4-DMAP or pyridine.

Selective esterification of Compound A is performed by a variety of methods known to the skilled artisan. In one method, the alcohol is first esterified with a trichloroethyl derivative (e.g., mono-trichloroethyl succinate). After chromatographic isolation of the preferred ester, reductive elimination of the tricholoroethyl group is carried out by reaction with zinc dust in acetic acid. Alternatively, another method of selective esterification is the hydrolysis of the bis-ester.

It is understood that, unless expressly stated to the contrary or otherwise clear from the context, a reference to a compound per se employed in the combination of the present invention implicitly refers to the free compound, a pharmaceutically acceptable salt thereof, and/or a pharmaceutically acceptable ester thereof.

The combination of compounds of the present invention is useful in the inhibition of HIV protease, the inhibition of HIV reverse transcriptase, the prevention or treatment of infection by human immunodeficiency virus (HIV) and the prevention or treatment of consequent pathological conditions such as AIDS. Treating AIDS or preventing or treating infection by HIV is defined as including, but not limited to, treating a wide range of states of HIV infection: AIDS, ARC, both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

For these purposes, the combinations of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of each compound in the combination of the present invention.

These pharmaceutical compositions may be in the form of orally-administrable suspensions, capsules or tablets; nasal sprays; sterile injectable preparations, for example, as sterile injectable aqueous or oleaginous suspensions or suppositories.

In accordance with the method of the present invention, the individual components of the combination can be administered separately at different times during the course of therapy or concurrently in divided or single combination forms. For example, in a two-component combination which is the HIV protease inhibitor, Compound A, and the non-nucleoside HIV reverse transcriptase inhibitor, DMP-266, treatment with DMP-266 can commence prior to, subsequent to or concurrent with commencement of treatment with Compound A. The instant invention is therefore to be understood as embracing all such regimes of simultaneous or alternating treatment and the term "administering" is to be interpreted accordingly.

In the method of the present invention, the combination of Compound A and Indinavir, and optionally with one or more of the other antiviral compounds (e.g., Saquinavir), are preferably administered concurrently in divided or single combination forms. In another preferred embodiment of the method of the invention is administration, preferably concurrent administration, of the combination of Compound A and Indinavir with food (e.g., a high-fat meal). The term "with food" means the consumption of a meal either during or no more than about one hour before or after administration of the combination of Compound A with one or more of the other antiviral compounds.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The oral administration of a composition comprising Compound A and Indinavir, or a pharmaceutically acceptable salt or ester of either or both, is suitably accomplished by uniformly and intimately blending together a suitable amount of each compound in the form of a powder, optionally also including a finely divided solid carrier, and encapsulating the blend in, for example, a hard gelatin capsule. The solid carrier can include one or more substances which act as binders, lubricants, disintegrating agents, coloring agents, and the like. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Oral administration of a composition comprising a combination of Compound A and Indinavir in suitable proportions can also be accomplished by preparing capsules or tablets containing the desired amount of Compound A only, optionally blended with a solid carrier as described above, and capsules containing the desired amount of Indinavir only (e.g., CRIXIVAN® capsules). Compressed tablets containing Compound A can be prepared by uniformly and intimately mixing the active ingredient with a solid carrier such as described above to provide a mixture having the necessary compression properties, and then compacting the mixture in a suitable machine to the shape and size desired. Molded tablets may be made by molding in a suitable machine, a mixture of powdered Compound A moistened with an inert liquid diluent. Oral administration can also be accomplished by preparing compressed or molded tablets containing Compound A as just described, the tablets of suitable size for insertion into standard capsules (e.g., hard gelatin capsules), and then inserting the tablets into capsules containing a suitable amount of Indinavir powder.

The compounds of this invention can be administered to humans in dosage ranges specific for each compound. Compound A, or a pharmaceutically acceptable salt or ester thereof, has dosage levels of the order of 0.02 to 5.0 or 10.0 grams-per-day (e.g., of the order of 0.1 to 10.0 grams-per-day) that are useful in the treatment or prevention of the above indicated conditions, with oral doses two-to-five times higher. For example, infection by HIV is effectively treated by the administration of from 1.0 to 50 milligrams of Compound A per kilogram of body weight from one to four times per day. As another example, HIV infection may be effectively treated by the administration of from 2 to 200 milligrams of Compound A per kilogram of body weight from one to four times per day. In one preferred regimen, dosages of 100–800 mg every six hours are administered orally to each patient. Zidovudine, or a pharmaceutically acceptable salt thereof, is administered orally at a dosage range between about 2.0 to 15.0 mg/kg given two to four times per day. Preferably, Zidovudine, or a pharmaceutically acceptable salt or ester thereof is administered orally at a dosage of about 300 mg twice daily, or 100 mg every four hours while awake. Stavudine, or a pharmaceutically acceptable salt thereof, is administered orally at a dosage between about 0.3 to 0.7 mg/kg, given two to four times per day. Preferably, Stavudine, or a pharmaceutically acceptable salt thereof, is administered orally to each patient at a dosage of about 40 mg twice daily if the patient has a mass of 60 kg or greater. If the patient's mass is under 60 kg, Stavudine is administered orally at a dosage of about 30 mg twice daily. Lamivudine, or a pharmaceutically acceptable salt thereof, is administered orally to each patient at a dosage of about 2.0 to 10.0 mgs/kg, given two to four times per day. Preferably, Lamivudine, or a pharmaceutically acceptable salt thereof, is administered orally to each patient at a dosage of about 150 mg twice daily. DMP-266, or a pharmaceutically acceptable salt thereof, is administered orally to each patient at a dosage range between about 1 to 100 mg/kg body weight in divided doses. Preferably, DMP-266 or a pharmaceutically acceptable salt thereof is administered orally to each patient at a dosage between 400–800 mgs once per day or 100–500 mgs twice per day. Ritonavir, or a pharmaceutically acceptable salt thereof, is administered orally at a dosage between about 200 mg and 1000 mg administered three times per day. Preferably, Ritonavir, or a pharmaceutically acceptable salt thereof, is administered orally at a dosage of about 600 mg twice daily. Nelfinavir, or a pharmaceutically acceptable salt or ester thereof, is administered in single or divided doses at a level of about 0.01 mg/kg to about 50 mg/kg of body weight. Preferably, daily doses are from about 0.05 mg/kg to about 20 mg/kg of body weight. More preferably, it is administered orally to each patient at a dosage of about 750 mg, given three times a day. Abacavir, or a pharmaceutically acceptable salt thereof, is administered orally to each patient at a dosage range between about 3 to 120 mg/kg of body weight per day, given in two, three, or four sub-doses daily. Preferably, Abacavir, or a pharmaceutically acceptable salt or ester thereof, is administered in the range of 6 to 90 mg/kg of body weight per day, more preferably in the range of 15 to 60 mg/kg of body weight per day, given two, three, or four times daily. Indinavir, or a pharmaceutically acceptable salt or ester thereof, is administered orally to each patient at a dosage range of about 1.0 to 50 mg/kg of body weight given one to four times a day. Preferably, it is administered at about 400–600 mg every six hours, and most preferably administered in a dosage of about 800 mg, given every eight hours. 141-W94, or a pharmaceutically acceptable salt or ester thereof, is administered orally to each patient at a dosage range of between 1000–1400 mg twice daily or between 600–1000 mg three times daily. Delavirdine, or a pharmaceutically acceptable salt or ester thereof, is administered orally to each patient at a dosage range between 200 and 600 mg three times daily. Saquinavir, or a pharmaceutically acceptable salt thereof, is administered orally three times per day at a dosage range of between about 200 mg and 1000 mg. Preferably, it is administered at about 400–800 mg every six hours, and most preferably administered in a dosage of about 600 mg, given every eight hours.

When Compound A and Indinavir are administered in combination, the weight ratio of Compound A to Indinavir is suitably in the range of from about 15:1 to about 1:15, typically from about 10:1 to about 1:10, and more typically from about 8:1 to about 1:8. Also useful are weight ratios of Compound A to Indinavir ranging from about 6:1 to about 1:6, or from about 4:1 to about 1:4 (e.g., from about 3:1 to about 1:2), or from about 2:1 to about 1:2, or from about 1.5:1 to about 1:1.5. In one aspect, the amount by weight of Compound A is equal to or greater than that of Indinavir, wherein the weight ratio of Compound A to Indinavir is suitably in the range of from about 1:1 to about 15:1, typically from about 1:1 to about 10:1, and more typically from about 1:1 to about 8:1. Also useful are weight ratios of Compound A to Indinavir ranging from about 1:1 to about 6:1, or from about 1:1 to about 5:1, or from about 1:1 to about 4:1 (e.g., from about 3:2 to about 3:1), or from about 1:1 to about 2:1 (e.g., about 1.5:1), or from about 1:1 to about 1.5:1.

In one embodiment, Compound A and Indinavir are co-administered orally twice a day, wherein the amount of Compound A per dose is from about 150 to about 1500 mg, and the amount of Indinavir per dose is from 450 to about 1500 mg. In another embodiment, the amounts per dose for twice daily oral co-administration are from about 200 to about 1000 mg of Compound A and from about 600 to about 1200 mg of Indinavir. In still another embodiment, the amounts per dose for twice daily oral co-administration are from about 400 to about 800 mg of Compound A and from about 600 to about 1200 mg of Indinavir. Exemplary combinations of Compound A (mg)/Indinavir (mg) for twice daily dosage include 200/600, 400/600, 600/600, 800/600, 1000/600, 200/666, 400/666, 600/666, 800/666, 1000/666, 1200/666, 200/800, 400/800, 600/800, 800/800, 1000/800, 1200/800, 200/1200, 400/1200, 600/1200, 800/1200, 1000/1200, and 1200/1200.

In another embodiment, Compound A and Indinavir are co-administered orally once a day, wherein the amount of Compound A per dose is from about 200 to about 1600 mg, and the amount of Indinavir per dose is from 200 to about 1600 mg. Another embodiment is the once daily oral co-administration of from about 400 to about 1600 mg of Compound A and from about 400 to about 1600 mg of Indinavir. Exemplary combinations of Compound A (mg)/Indinavir (mg) for once daily dosage include 200/600, 400/600, 600/600, 800/600, 1000/600, 1200/600, 1400/600, 1600/600, 200/666, 400/666, 600/666, 800/666, 1000/666, 1200/666, 1400/666, 1600/666, 200/800, 400/800, 600/800, 800/800, 1000/800, 1200/800, 1400/800, 1600/800, 200/1200, 400/1200, 600/1200, 800/1200, 1000/1200, 1200/1200, 1400/1200, 1600/1200, 200/1600, 400/1600, 600/1600, 800/1600, 1000/1600, 1200/1600, 1400/1600, and 1600/1600.

It will be understood, however, that specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the instant specification, particularly the Schemes and Examples, are as follows:

Aq=aqueous
Ac=acetyl
EtOH=ethanol
IPAc=isopropyl acetate
t-Bu=tertiary butyl
HPLC=high performance liquid chromatography
ECG=electrocardiogram The following examples are provided to further define the invention without, however, limiting the invention to the particulars of these examples.

EXAMPLE 1

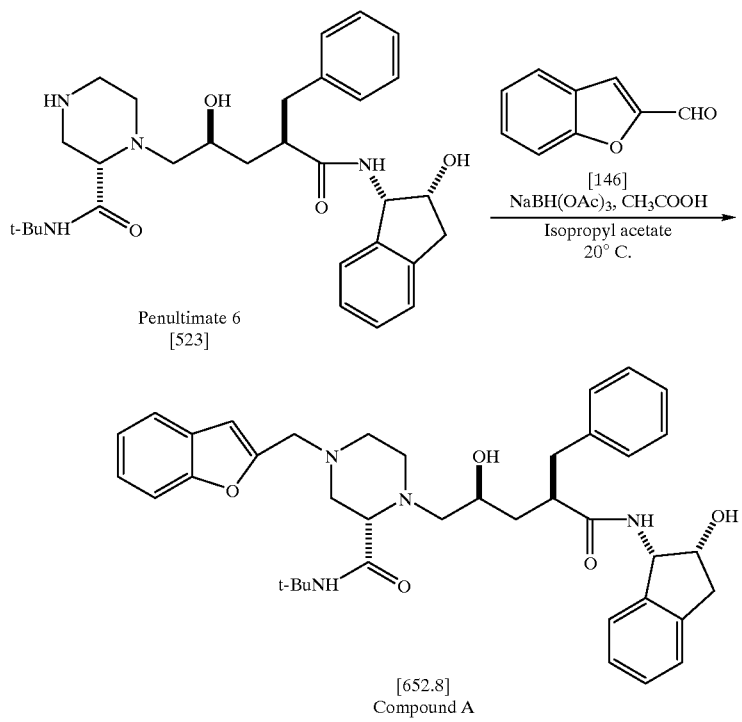

Penultimate 6
[523]

[652.8]
Compound A

The IPAc/methanol solution (about 20% methanol in isopropyl acetate) containing the penultimate intermediate (70.7 L, 8.66 mol, 4.53 kg) is concentrated in vacuo (25–46° C., 100 mm Hg) at about 20 L constant volume while adding fresh IPAc to perform a constant volume solvent switch to EPAc from the methanol/IPAc mixture. A final volume of 44L and KF (Karl Fisher) titration for water of 994 mg/L is obtained. An NMR spectrum indicated no detectable methanol. Benzofuran 2-carboxaldehyde (1.49 kg, 9.70 mol) is added in one portion at 22–23° C. and 500 mL IPAc rinse was added. Sodium triacetoxyborohydride is charged as a solid over 10–15 min (2.90 kg, 13.0 mol) in one portion at ambient temperature and followed by a 500 mL IPAc flush. Glacial acetic acid is added (495 mL) at 27–28° C. and the mixture was aged for 2.5 h at 20–21° C. The reaction was quenched by the addition of 8 L of 13.8% aqueous $KHCO_3$ solution, evolution of gas (hydrogen) is observed. The combined batch is added to an extractor and additional aq $KHCO_3$ solution (16 L) and IPAc (15 L) is added. The mixture is agitated and the layers are separated and the IPAc phase is washed with additional aq $KHCO_3$ solution (24 L) then washed with 3×24 L deionized water. The washed crude Compound A free base solution is then combined with a similar solution resulting from parallel processing of an identically sized batch, and a constant volume distillation at 52 L was conducted at 15–18 in/Hg pressure with a batch temperature of 55–62° C. to a final KF of 330 mg/L. The resulting thick slurry was cooled from 60° C. to 3° C. over 4 h and the solids were isolated using a 23 inch filter pot; the cake was washed with cold 10° C. IPAc (10 L total) and the wet solid dried in a vacuum oven at 20° C.; 25–28 in/Hg with a nitrogen sweep to yield the Compound A freebase.

EXAMPLE 2

Benzofuran-2-carbinol Preparation

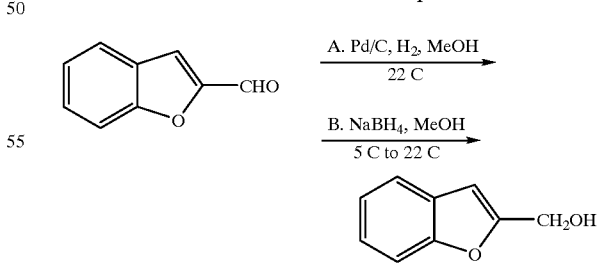

Method A

Benzofuran-2-carboxaldehyde (10.0 g, 68 mmol) was dissolved in methanol (90 mL). 5% Pd/C (0.500 g) was charged and the reaction mixture was hydrogenated for 4.5 hours at 40 psi $H_2$. The reaction was judged complete by tlc (4:1 hexanes/EtOAc) and the solution was filtered to remove the Pd/C and concentrated in vacuo to provide benzofuran-2-carbinol as an oil.

Method B

Benzofuran-2-carboxaldehyde (10.0 g, 68 mmol) was dissolved in methanol (70 mL) and cooled to 5 C. Sodium borohydride (2.58 g, 68 mmol) was charged portionwise at 5 C. The batch was aged at 5 C. for 40 minutes and allowed to warm to room temperature (22 C.). The reaction was judged complete by tlc (4:1 hexanes/EtOAc) and the reaction mixture was cooled to 5 C. DI water (20 mL) was charged and the solution was concentrated in vacuo. EtOAc (80 ml) was charged and the solution was washed with DI water (2×20 mL). The EtOAc layer was concentrated in vacuo to provide benzofuran-2-carbinol as an oil.

EXAMPLE 3

Benzofuran-2-carbinol Preparation

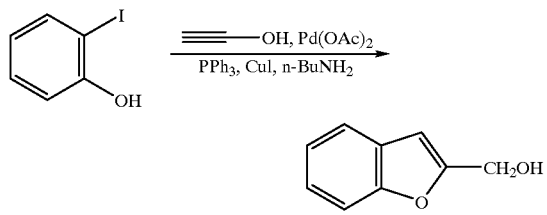

2-Iodophenol (500 mg, 2.27 mmol), propargyl alcohol (265 μl, 4.54 mmol), Pd(OAc)$_2$, (5.1 mg, 0.03 mmol), triphenylphosphine (12 mg, 0.046 mmol), n-butylamine (450 μL, 4.5 mmol) and CuI (8.6 mg, 0.045 mmol) were combined in 4.5 mL of THF and the mixture was heated at 40° C. under nitrogen for 36 h. The mixture was cooled to room temperature and the solvents were removed in vacuo and the residue purified by SiO$_2$ column chromatography on 100 g of silica gel, eluting with 20% ethyl acetate in hexanes. 2-(Hydroxymethyl)benzofuran was obtained by concentration of the product containing fractions. [Kudu, N. G.; Pal, M.; Mahanty, J. S.; Dasgupta, F. K. JCS Chem. Com. 1992, 41]

EXAMPLE 4

Benzofuran-2-chloromethyl Preparation

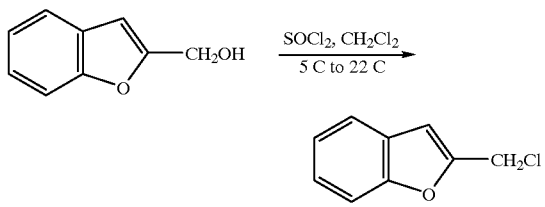

Method A

Benzofuran-2-carbinol (10.38 g, 68.4 mmol) was dissolved in methylene chloride (100 mL) and cooled to 5 C. Thionyl chloride (5.49 mL, 75.2 mmol) was charged over 5 minutes and the reaction mixture was aged at 5 C. for 30 minutes and allowed to warm to 22 C. The reaction mixture was aged at 22 C. for 4 hours. The methylene chloride batch was washed with DI water (4×60 mL) and filtered through silica gel. The solution was concentrated in vacuo to provide a solid upon cooling. The crude solid was dissolved in hexanes (120 mL) and treated with Darco G-60 (1.0 g). The slurry was filtered and the solution was concentrated in vacuo to provide the benzofuran-2-chloromethyl compound as a solid.

EXAMPLE 5

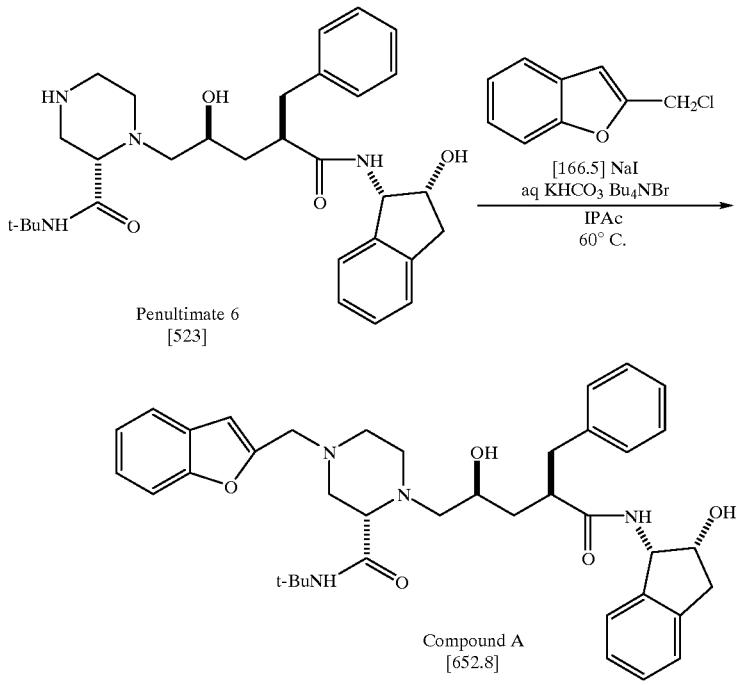

The isolated penultimate solid (13.1 g, 25 mmol) was combined with IPAc (60 mL), water 20 mL), KHCO₃ (4.25 g, 42.5 mmol), sodium iodide (1.88 g, 12.5 mmol) and tetrabutylammonium bromide (600 mg, 1.86 mmol) and the mixture heated to 45° C. under nitrogen atmosphere. 2-(Chloromethyl)benzofuran (4.6 g, 27.5 mmol) was added and the resulting mixture was heated to 59–61° C. for 5 h. The mixture was allowed to cool to room temperature and diluted with IPAc (100 mL) and the aqueous layer was separated. The organic layer was washed with 3×50 mL water, then 50 mL brine solution and dried (MgSO₄) and the filtrate concentrated in vacuo and flushed with 100 mL IPAc and concentrated atmospherically to 80 mL, cooled to 25° C., seeded and aged with agitation for 2 h. The solids were filtered and washed with cold IPAc (2×15 mL) to afford Compound A free base.

EXAMPLE 6

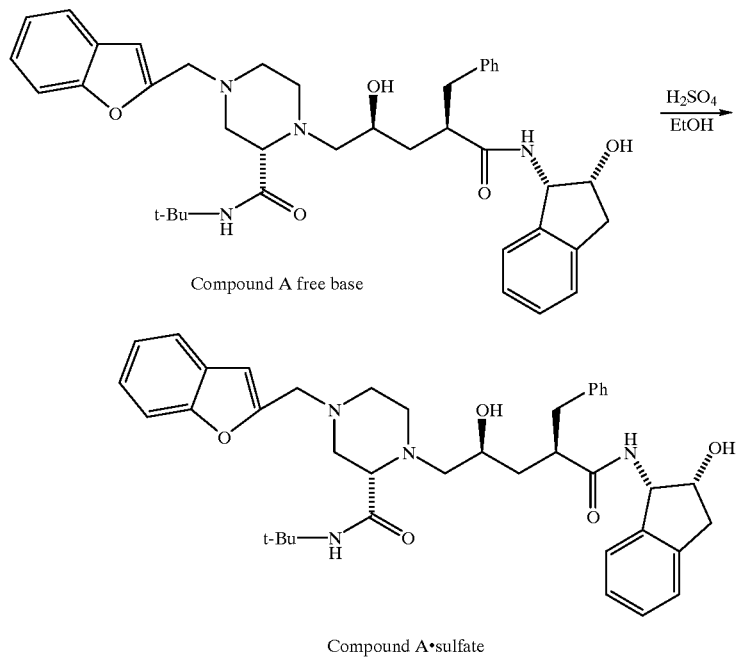

The Compound A freebase (25 g, 38.3 mmol) was dissolved in absolute ethanol (150 mL) at 22° C. The batch was filtered through a 5 μm filter and the filter flushed with absolute ethanol (50 mL). A solution of sulfuric acid/ethanol was prepared at <5° C. by charging concentrated sulfuric acid (3.91 g, 38.3 mmol) into a cooled solution (<5° C.) of absolute ethanol (50 mL) at such a rate that the temperature remained <5° C. A portion of the acid solution (10 mL, 20 vol %) was charged into the Compound A batch solution at 22° C. The Compound A batch may or may not be seeded at this point with Compound A.sulfate.ethanolate (500 mg) at 22° C. Ideally, the Compound A batch was seeded, as seeding relieves supersaturation during crystallization. The slurry was aged at 20–25° C. for 30 minutes. The remainder of the acid solution was charged into the batch via canula over 60 minutes. The batch temperature remained 20–25° C. during the addition (note: the acid solution was held at <°5 C.) The final batch slurry was aged at 20– 25° C. for 60 minutes and filtered. The cake was washed with absolute ethanol (2×25 mL) and dried in vacuo (25" Hg, 20 C.) for 18 hours with a nitrogen bleed to afford the Compound A sulfate. The sulfate salt is characterized by differential scanning calorimetry (DSC) curve, at a heating rate of 10° C./min in an open cup under flowing nitrogen exhibiting an endotherm with an extrapolated onset temperature of about 190° C., a peak temperature of about 193° C. and an associated heat of about 120 J/gm. Based on results of TG and TG-FTIR, the endotherm is due to the combination of the loss of the ethanol and melting with decomposition. The x-ray powder diffraction pattern is characterized by d-spacings of 11.72, 5.56, 5.20, 5.00, 4.60, 4.50, 4.40, 4.26, 4.17, 4.08, 3.90, 3.81, 3.69, 3.24 and 3.33 Å.

EXAMPLE 7

As a specific embodiment of an oral composition, 100 mg of the compound of Example 6 and 50 mg of DMP-266 is formulated with sufficient finely divided lactose to provide a total amount of 580 to 590 mg to fill a size O hard gel capsule.

EXAMPLE 8

Protocol for Pharmacokinetic Evaluation of Combination Therapy with Compound A and DMP-266

This is a fixed-sequence, randomized, two-period, parallel protocol to measure the effect of DMP-266 on the pharmacokinetics and safety and tolerability of Compound A, an HIV-1 protease inhibitor, in seronegative patients. The pharmacokinetics and safety of a single 600 mg oral dose of Compound A is measured at baseline (Period I) and again (Period II) following administration of DMP-266 at 600 mgs once daily or 300 mgs twice daily (or a placebo instead of DMP-266) for six days. The study design is outlined in detail in the Table. Plasma concentration of Compound A is determined at 0, 0.5, 1, 1.5, 2, 3, 4, 6, 8, 10 and 12 hours following the dose. Laboratory safety is measured at predose and 12 hours after Compound A on Day 1.

Total plasma clearance of Compound A is calculated as the dose divided by the total area under the plasma concentration-time curve from zero to infinity. The apparent half-life is estimated from the slope of the terminal phase fitted to the log plasma concentration-time curve by the method of least squares. The concentration of Compound A in plasma or plasma filtrate is determined by analysis on HPLC, monitored for absorbance at 220 nm.

TABLE 1

| Period I (day O) | |
| --- | --- |
| Period I (day 1)-Compound A pharmacokinetics | Compound A single 600 mg dose plasma profile (12 h) |
| Period I-to-II- interim treatment (days 2–7) | DMP-266 mg 600 mg each day |

EXAMPLE 9

Protocol for Combination Therapy with Compound A and DMP-266

In this protocol to show the antiviral activity of one regimen of Compound A given with DMP-266 in HIV-seronegative subjects, Compound A is administered at a dose of 1200 mg two times a day and DMP-266 is administered at 300 mg two times a day. Antiviral activity is measured before and during combination therapy by measuring serum levels of the HIV p24 antigen, serum levels of HIV RNA, and CD4 lymphocyte counts.

EXAMPLE 10

Pharmacokinetic Study of Compound A in Healthy Human Males

A double-blind, single-rising dose, alternating two-panel, four-period, placebo-controlled study was conducted for Compound A in healthy adult males in the fasted state. Single doses of 20, 50, 100, 200, 400, 800 and 1200 mg of Compound A, or placebo, were administered as an oral suspension of the sulfate salt form of Compound A in sterile water. Each subject received increasing single oral doses of Compound A or placebo during each of the four treatment periods in alternate panels. Panel A dosage levels were 20, 100, 400 mg, and 400 mg with food. Panel B dosage levels were 50, 200, 800 and 1200 mg. For each period, 6 subjects received Compound A and 2 subjects received placebo as allocated by a randomized schedule. In Panel A, subjects who received 400 mg of Compound A also received 400 mg of Compound A with food. The safety of the subjects was monitored prior and subsequent to dosing by clinical adverse event reporting, measurement of vital signs, physical examinations, blood and urine laboratory safety tests, and ECGs. Plasma concentrations of Compound A were determined predose and at 0.5, 1, 1.5, 2, 3, 4, 6, 10, 12, 24, 32 and 48 hours following each single dose in each period, using a reverse-phase HPLC column switching method with fluorescence detection. Pharmacokinetic parameters determined during the study are shown in the following Table.

TABLE 2

| Dose (mg) | $C_{max}$ (nM) | $T_{max}$ (hr) | AUC ($\mu M \cdot hr$) | $C_{8\,hrs}$ (nM) | $C_{12\,hrs}$ (nM) |
| --- | --- | --- | --- | --- | --- |
| 50 | 12 (64) | 0.6 | — | — | — |
| 100 | 36 (51) | 0.5 | — | — | — |
| 200 | 85 (68) | 0.7 | 0.24 (82) | 5 (—) | — |
| 400 | 166 (72) | 1.8 | 0.66 (68) | 15 (—) | 6 (—) |
| 400w/food | 170 (75) | 4.0 | 0.80 (56) | 32 (47) | 7 (—) |

TABLE 2-continued

| Dose (mg) | $C_{max}$ (nM) | $T_{max}$ (hr) | AUC ($\mu M \cdot hr$) | $C_{8\,hrs}$ (nM) | $C_{12\,hrs}$ (nM) |
| --- | --- | --- | --- | --- | --- |
| 800 | 568 (45) | 2.6 | 3.09 (54) | 126 (102) | 45 (82) |
| 1200 | 1354 (125) | 2.1 | 7.28 (124) | 338 (130) | 128 (130) |

The $C_{max}$ denotes the maximum plasma concentration of Compound A.
$C_{8\,hrs}$ and $C_{12\,hrs}$ denote the concentrations of Compound A in the plasma at 8 and 12 hours respectively after dosing.
AUC denotes the area under the curve of plasma concentration versus time.
Each of the values reported for $C_{max}$, $T_{max}$, AUC, $C_{8\,hrs}$ and $C_{12\,hrs}$ is the arithmetic mean for the six subjects. The parenthetical values indicate coefficient of variation in percent.
"—" denotes values could not be determined, because plasma concentrations fell below the assay quantification limit.
Values for 20 mg dose are not shown because plasma concentrations fell below the assay quantification limit.

EXAMPLE 11

Pharmacokinetic Study of Compound A Alone and in Combination with Indinavir in Healthy Human Males A double-blind, single-rising dose, alternating two-panel, four-period, placebo-controlled study was conducted for Compound A alone and in combination with Indinavir in healthy adult males in the fasted state. In Panel A, each subject received an oral dose of 1600 mg of Compound A, or placebo, in the first period; followed in the next period by a 200-mg single oral dose of Compound A, or placebo, co-administered with a single 800-mg oral dose of Indinavir; followed by 400 mg of Compound A, or placebo, plus 800 mg of Indinavir in the third period; and then by 200 mg of Compound A, or placebo, plus 1200 mg of Indinavir in the fourth period. In Panel B, each subject received an oral dose of 2000 mg of Compound A, or placebo, in the first period; followed in the next period by a 600-mg single oral dose of Compound A, or placebo; followed by 600 mg of Compound A, or placebo, plus 800 mg of Indinavir in the third period; and then by 600 mg of Compound A, or placebo, in the fourth period. All of the doses of Compound A were administered as the sulfate salt form of Compound A. All of the Compound A doses were oral suspensions of the sulfate salt form in sterile water, except that the 600-mg doses administered to Panel B in the fourth period were tablets. Indinavir was administered in the form of CRIXIVAN® capsules. The safety of the subjects was monitored prior and subsequent to dosing by clinical adverse event reporting, measurement of vital signs, physical examinations, blood and urine laboratory safety tests, and ECGs. Plasma concentrations of Compound A were determined predose and at 0.5, 1, 1.5, 2, 3, 4, 6, 8, 12, 16, 20, 24, 30, 36 and 48 hours following each single dose in each period, using a reverse-phase HPLC column switching method with fluorescence detection. Pharmacokinetic parameters determined during the study are shown in the following Table.

TABLE 3

| Comp'd A Dose (mg) | n | Cmax (nM) | Tmax (hr) | AUC ($\mu M \cdot hr$) | $C_{8\,hrs}$ (nM) | $C_{12\,rs}$ (nM) | $C_{24\,hrs}$ (nM) |
| --- | --- | --- | --- | --- | --- | --- | --- |
| 600 (tablets) | 8 | 211 | 1.5 | 1.42 (68) | 50 | 38 | 17 |
| 600 | 8 | 208 | 1.4 | 1.41 (42) | 55 | 39 | 13 |
| 1600 | 6 | 613 | 2 | 4.72 (40) | 163 | 93 | 46 |
| 2000 | 8 | 1267 | 2.5 | 10.43 (50) | 444 | 250 | 105 |
| 200 + 800 IDV | 6 | 1576 | 2.2 | 7.45 (8) | 232 | 70 | 8 |

TABLE 3-continued

| Comp'd A Dose (mg) | n | Cmax (nM) | Tmax (hr) | AUC (μM · hr) | $C_{8\ hrs}$ (nM) | $C_{12\ hrs}$ (nM) | $C_{24\ hrs}$ (nM) |
|---|---|---|---|---|---|---|---|
| 400 + 800 IDV | 6 | 2349 | 2.5 | 12.2 (20) | 399 | 124 | 20 |
| 600 + 800 IDV | 8 | 3884 | 3.3 | 25.22 (21) | 1193 | 352 | 65 |
| 200 + 1200 IDV | 6 | 1561 | 2.3 | 9.22 (30) | 416 | 107 | 10 |

IDV denotes Indinavir.
n is the number of subjects.
The $C_{max}$ denotes the maximum plasma concentration of Compound A.
$C_{8\ hrs}$, $C_{12\ hrs}$, and $C_{24\ hrs}$ denote the concentrations of Compound A in the plasma at 8, 12, and 24 hours respectively after dosing.
AUC denotes the area under the curve of plasma concentration versus time.
Each of the values reported for Cmax, $T_{max}$, AUC, $C_{8\ hrs}$, $C_{12\ hrs}$, and $C_{24\ hrs}$ is the arithmetic mean. The parenthetical values indicate coefficient of variation in percent.

A comparison of the results in Table 2 and Table 3 shows that the co-administration of Indinavir with Compound A substantially increased the Compound A plasma levels. The AUC of Compound A was about 30× higher for the co-administration of 200 mg of Compound A with 800 mg of Indinavir relative to the administration of 200 mg of Compound A alone. $C_{max}$ and $C_8$ hrs were also substantially higher; i.e., about 19× and 46× higher respectively. In the panel receiving 600 mg of Compound A in combination with 800 mg of Indinavir, the AUC was about 18-fold higher than for administration of Compound A alone. In addition to increasing the Compound A plasma levels, co-administration with Indinavir also reduced variability in the Compound A levels. The coefficients of variation for the AUCs in Table 2 range from 54 to 124%, whereas they range from 8 to 30% in the combination arms in Table 3.

EXAMPLE 12
Pharmacokinetic Study in Healthy Human Males of Compound A in Combination with Indinavir with and without Fasting As part of a double-blind, placebo-controlled study, each of eight members of a panel of ten healthy adult males received 600 mg (3×200-mg tablets) of Compound A orally in combination with 666 mg (2×333 mg capsules) of Indinavir orally, and the remaining two members each received a placebo to Compound A in combination with 666 mg of Indinavir. All of the subjects received the regimen once in the fasted state and once with a high-fat breakfast. The two single-dose treatments (fasted, fed) were administered in randomized crossover fashion, separated by one week. For treatments with food a breakfast consisting of two eggs, two strips of bacon, toast with two pats of butter (2×12.5 g), 120 g of fried potatoes and 240 ml of whole milk were consumed in no more than 15 minutes, and the test medication was administered within 5 minutes after completion of the breakfast.

All of the doses of Indinavir were administered in the form of two 333.3-mg Crixivan® capsules. All of the doses of Compound A were administered as the sulfate salt form of Compound A. All of the Compound A doses were tablets containing 200 mg of Compound A. Other ingredients in the tablets included microcrystalline cellulose (Avicel PH 101), mannitol SD 200, croscarmellose sodium, hydroxypropyl cellulose and magnesium stearate. The tablets were film coated with a suspension of hydroxypropyl methylcellulose, hydroxypropyl cellulose and titanium dioxide.

The safety of the subjects was monitored prior and subsequent to dosing by clinical adverse event reporting, measurement of vital signs, physical examinations, blood and urine laboratory safety tests, and ECGs. Plasma concentrations of Compound A were determined predose and at 0.5, 1, 1.5, 2, 3, 4, 6, 8, 12, 16, 20, 24, 30, 36 and 48 hours following each single dose in each period, using a reverse-phase HPLC column switching method with fluorescence detection. Pharmacokinetic parameters determined during the study are shown in the following Table.

TABLE 4

| Comp'd A Dose (mg) | n | Cmax (nM) | $T_{max}$ (hr) | AUC (μM · hr) | $C_{8\ hrs}$ (nM) | $C_{12\ hrs}$ (nM) | $C_{24\ hrs}$ (nM) |
|---|---|---|---|---|---|---|---|
| 600 + 666 IDV (fasted) | 7 | 2915 | 2.6 | 15.73 (36) | 583 | 188 | 37 |
| 600 + 666 IDV (fed) | 7 | 4232 | 3.7 | 25.32 (26) | 1323 | 433 | 58 |

IDV denotes Indinavir.
n is the number of subjects. One of the eight subjects was dosed separately and later than the rest of the group and his results are not included herein.
The $C_{max}$ denotes the maximum plasma concentration of Compound A.
$C_{8\ hrs}$, $C_{12\ hrs}$, and $C_{24\ hrs}$ denote the concentrations of Compound A in the plasma at 8, 12, and 24 hours respectively after dosing.
AUC denotes the area under the curve of plasma concentration versus time.
Each of the values reported for $C_{max}$, $T_{max}$, AUC, $C_{8\ hrs}$, $C_{12\ hrs}$, and $C_{24\ hrs}$ is the arithmetic mean. The parenthetical values indicate coefficient of variation in percent.

The results in Table 4 unexpectedly show that the co-administration of Compound A and Indinavir with food (i.e., in the fed state) provided higher Compound A plasma levels than for co-administration of Compound A and Indinavir without food (in the fasted state).

What is claimed is:
1. A synergistic composition comprising (a) Compound A of the formula

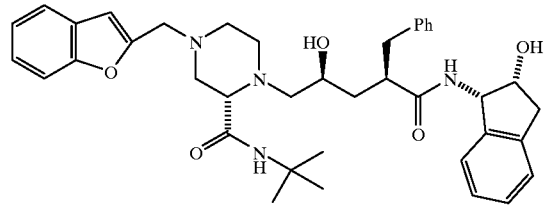

or a pharmaceutically acceptable salt or ester thereof and (b) a compound selected from the group consisting of Indinavir, and pharmaceutically acceptable salts and esters thereof.

2. The composition of claim 1, wherein (a) is the sulfate salt of Compound A and (b) is the sulfate salt of Indinavir.

3. The composition of claim 1, having a weight ratio of Compound A to Indinavir of from about 2:1 to about 1:2.

4. The composition of claim 1, having a weight ratio of Compound A to Indinavir of from about 1:1 to about 2:1.

5. The composition of claim 1, further comprising (c) Zidovudine or a pharmaceutically acceptable salt or ester thereof and (d) Lamivudine or a pharmaceutically acceptable salt or ester thereof.

6. The composition of claim 1, further comprising (c) Stavudine or a pharmaceutically acceptable salt or ester thereof and (d) Lamivudine or a pharmaceutically acceptable salt or ester thereof.

7. The composition of claim 1, further comprising (c) DMP-266 or a pharmaceutically acceptable salt or ester thereof.

8. The composition of claim 1, further comprising (c) Delavirdine or a pharmaceutically acceptable salt or ester thereof.

9. The composition of claim 1, further comprising (c) Saquinavir or a pharmaceutically acceptable salt or ester thereof.

10. The composition of any one of claims 5 to 9, having a weight ratio of Compound A to Indinavir of from about 2:1 to about 1:2.

11. The composition of any one of claims 5 to 9, having a weight ratio of Compound A to Indinavir of from about 1:1 to about 2:1.

12. A method of treating infection by HIV, which comprises administering to a subject in need thereof a therapeutically effective amount of the composition of claim 1.

13. The method of claim 12, wherein the weight ratio of Compound A to Indinavir is from about 2:1 to about 1:2.

14. The method of claim 12, wherein the weight ratio of Compound A to Indinavir is from about 1:1 to about 2:1.

15. A method of treating AIDS, which comprises administering to a subject in need thereof a therapeutically effective amount of the composition of claim 1.

16. The method of claim 15, wherein the weight ratio of Compound A to Indinavir is from about 2:1 to about 1:2.

17. The method of claim 15, wherein the weight ratio of Compound A to Indinavir is from about 1:1 to about 2:1.

18. A pharmaceutical composition comprising the composition of claim 1 and a pharmaceutically acceptable carrier.

19. The pharmaceutical composition of claim 18, wherein the weight ratio of Compound A to Indinavir is from about 2:1 to about 1:2.

20. The pharmaceutical composition of claim 18, wherein the weight ratio of Compound A to Indinavir is from about 1:1 to about 2:1.

* * * * *